(12) United States Patent
Mukai et al.

(10) Patent No.: US 9,125,773 B2
(45) Date of Patent: Sep. 8, 2015

(54) DISPOSABLE WEARING ARTICLE

(75) Inventors: Hirotomo Mukai, Kagawa (JP); Takaya Arayama, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 413 days.

(21) Appl. No.: 13/580,534

(22) PCT Filed: Feb. 25, 2011

(86) PCT No.: PCT/JP2011/001121
§ 371 (c)(1),
(2), (4) Date: Oct. 12, 2012

(87) PCT Pub. No.: WO2011/105108
PCT Pub. Date: Sep. 1, 2011

(65) Prior Publication Data
US 2013/0041336 A1   Feb. 14, 2013

(30) Foreign Application Priority Data
Feb. 27, 2010   (JP) .................................. 2010-043594

(51) Int. Cl.
*A61F 13/20*   (2006.01)
*A61F 13/535*   (2006.01)
(Continued)

(52) U.S. Cl.
CPC ............ *A61F 13/535* (2013.01); *A61F 13/4704* (2013.01); *A61F 13/49001* (2013.01); *A61F 13/53436* (2013.01)

(58) Field of Classification Search
CPC ........... A61F 13/4704; A61F 13/49001; A61F 13/535; A61F 13/5355; A61F 13/536; A61F 13/534; A61F 13/53409; A61F 13/53418; A61F 13/53427; A61F 13/53436; A61F 13/53445; A61F 13/45; A61F 13/47236; A61F 13/47245; A61F 2013/53765; A61F 2013/53778; A61F 2013/53786; A61F 2013/530883; A61F 2013/4543; A61F 2013/455; A61F 2013/4556; A61F 2013/4568; A61F 2013/4587

USPC .................................. 604/358, 378–380, 383
See application file for complete search history.

(56) References Cited

U.S. PATENT DOCUMENTS 6,312,416 B1 * 11/2001 Brisebois et al. ........ 604/385.01
2002/0052587 A1 *  5/2002 Magnusson et al. .......... 604/378
(Continued)

FOREIGN PATENT DOCUMENTS

EP   0904755 A2   3/1999
JP      539691    10/1993
(Continued)

OTHER PUBLICATIONS

Office Action mailed Sep. 3, 2013, corresponds to Japanese patent application No. 2010-043594.
(Continued)

*Primary Examiner* — Lynne Anderson
*Assistant Examiner* — Bradley Philips
(74) *Attorney, Agent, or Firm* — Lowe Hauptman & Ham, LLP

(57) ABSTRACT

A disposable diaper has a central elastic member formed along the lengthwise direction L so that the absorber can be curved to be convex in the inward direction, and a pair of side slits formed along the lengthwise direction L so that the absorber can be curved to be convex in the outward direction. A thickness of the absorber at the central portion and at the side edge portions are smaller than a thickness of the absorber at the middle portions.

9 Claims, 12 Drawing Sheets

(51) Int. Cl.
*A61F 13/534* (2006.01)
*A61F 13/49* (2006.01)
*A61F 13/47* (2006.01)

(56) References Cited

U.S. PATENT DOCUMENTS

| | | | |
|---|---|---|---|
| 2005/0055000 A1* | 3/2005 | Ohnishi | 604/367 |
| 2006/0069371 A1* | 3/2006 | Ohashi et al. | 604/385.01 |
| 2006/0264859 A1 | 11/2006 | Tsuji et al. | |
| 2008/0140042 A1 | 6/2008 | Mukai et al. | |
| 2014/0338822 A1* | 11/2014 | Mukai et al. | 156/196 |

FOREIGN PATENT DOCUMENTS

| | | |
|---|---|---|
| JP | 2001190592 A | 7/2001 |
| JP | 200441311 A | 2/2004 |
| JP | 2004248705 | 9/2004 |
| JP | 2004248705 A | 9/2004 |
| JP | 3616077 | 11/2004 |
| JP | 3616077 B2 | 2/2005 |
| JP | 2005279082 | 10/2005 |
| JP | 2005279082 A | 10/2005 |
| JP | 2006115996 | 5/2006 |
| JP | 2006115996 A | 5/2006 |
| JP | 2006346439 | 12/2006 |
| JP | 2006346439 A | 12/2006 |
| JP | 200729507 A | 2/2007 |
| JP | 2010259724 | 11/2010 |
| JP | 2011104021 A | 6/2011 |
| JP | 2011177310 A | 9/2011 |
| WO | 9109582 | 7/1991 |
| WO | 2008069279 | 6/2008 |
| WO | 2008069279 A1 | 6/2008 |
| WO | 2010140678 | 12/2010 |

OTHER PUBLICATIONS

Office Action issued Jul. 13, 2014, corresponding to GCC patent application No. GC 2011-17864.
Extended European Search Report dated May 15, 2014, corresponds to European patent application No. 11747072.4.
Office Action mailed Jan. 6, 2014, corresponds to Chinese patent application No. 201180011214.3.
International Search Report and Written Opinion for PCT/JP2011/001121 mailed Apr. 19, 2011.
Office Action issued Jan. 30, 2015, corresponding to Australian patent application No. 2011219336.

* cited by examiner

DISPOSABLE WEARING ARTICLE

RELATED APPLICATIONS

The present application is a national phase of PCT/JP2011/001121, filed Feb. 25, 2011 and is based on, and claims priority from, Japanese Application Number 2010-043594, filed Feb. 27, 2010.

TECHNICAL FIELD

The present disclosure relates to a disposable wearing article in which a curve forming portion for curving an absorber is formed at the absorber.

BACKGROUND ART

In disposable wearing articles such as pant-type diapers, a variety of contrivances are made in order to improve the feeling of a wearer or prevent leakage of bodily waste. For example, there is known a pant-type diaper in which three curve forming portions are formed along a lengthwise direction of an absorber for absorbing bodily waste of a wearer (Japanese Patent Application Publication No. 2006-346439, for example).

Specifically, in this pant-type diaper, three slits are formed at the absorber, and peripheral portions of the slits each are curved. The central slit peripheral portion is formed to be convex toward an excretion portion of the wearer. In addition, a lateral slit peripheral portion is formed to be convex at an opposite side of the central slit peripheral portion. Namely, a cross-cross-sectional shape of the absorber along a widthwise direction of the absorber is deformed in a W-letter shape.

Thus, the convex portion of the absorber, which is formed by the central slit peripheral portion, easily comes into intimate contact with a wearer's excretion portion. In addition, bodily waste easily enters a concave portion which is formed by two outside slit peripheral portions to be thereby able to restrain bodily waste from coming into direct contact with the wearer's skin.

SUMMARY OF INVENTION

However, if an attempt is made to improve an absorption quantity in the above-described conventional pant-type diaper, the following problem occurs. That is, since an absorber is positioned in a state in which it is curved at a wearer's crotch portion, if the absorber is thickened in order to improve the absorption quantity, the wearer easily has an unconformable feeling in a case where the wearer closes his or her legs at the time of taking a standing position, for example.

In addition, if the absorber is thickened, a slit peripheral portion, in particular, a central slit peripheral portion cannot be curved sufficiently and then the absorber hardly comes into intimate contact with the wearer's excretion portion. Thus, there has still remained unsolved the problem that urine or watery stool or the like easily leaks to the outside while it goes along the wearer's skin.

Therefore, it is an object of the present invention to provide an absorber for a disposable wearing article, such as a pant-type diaper, further improving absorptive power while reducing an uncomfortable feeling due to thickness of an absorber, in a case where the absorber is curved.

A disposable wearing article according to the present invention includes an absorber having: a lengthwise direction; a widthwise direction which is orthogonal to the lengthwise direction; an inward direction which is oriented to a wearer; and an outer direction which is oriented to a side opposite to the inward direction. The absorber has, in a crotch portion region applied to a crotch portion of the wearer, a central portion which is formed at a central part of the absorber in the widthwise direction, a pair of side edge portions including a side edge of the absorber in the widthwise direction, and a pair of middle portions which are positioned between the central portion and the side edge portions; at the central portion, a central curve forming portion is formed along the lengthwise direction so that the absorber can be curved to be convex in the inward direction; at the middle portion, a pair of side curve forming portions are formed along the lengthwise direction so that the absorber can be curved to be convex in the outer direction; a top face of the absorber, which is formed to be convex in the inward direction by the central curve forming portion, is adapted to come into contact with the crotch portion, and a thickness of the absorber at the central portion is smaller than a thickness of the absorber at the middle portion According to the characteristics of the present invention, there can be provided a disposable wearing article, such as a pant-type diaper, featuring the absorber, further improving absorptive power while reducing an uncomfortable feeling due to thickness of the absorber, in a case where the absorber is curved to thereby improve a wearer's feeling or preventing leakage of bodily waste.

DESCRIPTION OF EMBODIMENT

Figure 1:
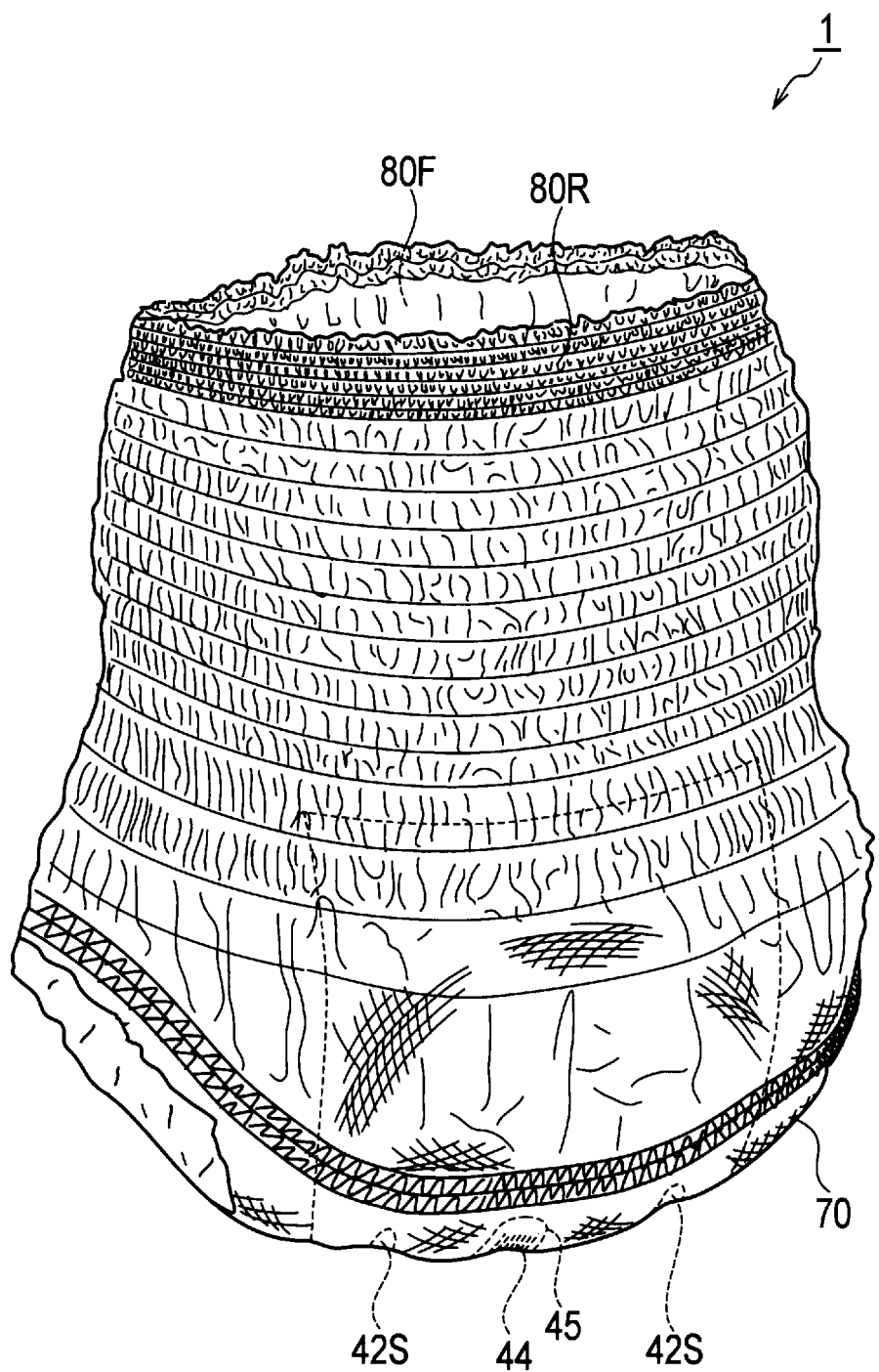
FIG. 1 is a schematic perspective view of a diaper 1 according to a first embodiment.

Next, embodiments of a disposable diaper 1 according to the present invention, will be described with reference to the drawings. Specifically, a first embodiment and a second embodiment and other embodiments will be described.

In the description of the drawings that follow, the same or like constituent elements are designated by the same or like reference numerals. However, it should be kept in mind that the drawings are schematic and ratios of dimensions each may be different from an actual one.

Therefore, specific dimensions or the like should be determined in consideration of the following description. In addition, portions with different dimensional interrelationships or ratios can be included in the drawings as well.

First Embodiment

A disposable wearing article according to the embodiment is provided with a central curve forming portion and a pair of side curve forming portions, and is characterized in that a thickness of the absorber at a central portion, which is a region including a position of the central curve forming portion, and a side edge portion, which is a region including a side edge of the absorber is smaller than that of the absorber at a middle portion including the position of the side curve forming portion.

(1) Entire Schematic Configuration of Disposable Wearing Article

FIG. 1 is a schematic perspective view of a disposable diaper 1, which comprises a disposable wearing article. As shown in FIG. 1, the disposable diaper 1 is a pant-type disposable diaper. The disposable diaper 1 is provided with: an exterior topsheet 70, a foreside exterior backsheet 80F and a backside exterior backsheet 80R which configure an exterior portion of the disposable diaper 1. An absorber 40 comprised of a cotton-like pulp and a highly polymerized water absorbent polymer (hereinafter, referred to as a water absorbent polymer) is provided inside (a skin contact surface side) of the external top sheet 70.

In the absorber 40, a central aperture 45 is formed at a center in a widthwise direction W. In addition, a central elastic member 44 is provided so as to be superimposed with the central aperture 45. One pair of side slits 42S is formed with a slit either side of the central aperture 45. By means of the elastic member and slits formed at the absorber 40, the absorber 40 is configured so that it can be curved when the disposable diaper 1 is worn. In the embodiment, the central elastic member 44 comprises a central curve forming portion, and the side slits 42S configure side curve forming portions. As will be readily appreciated by those skilled in the art, however, the curve forming portions may take other forms.

Figure 2:
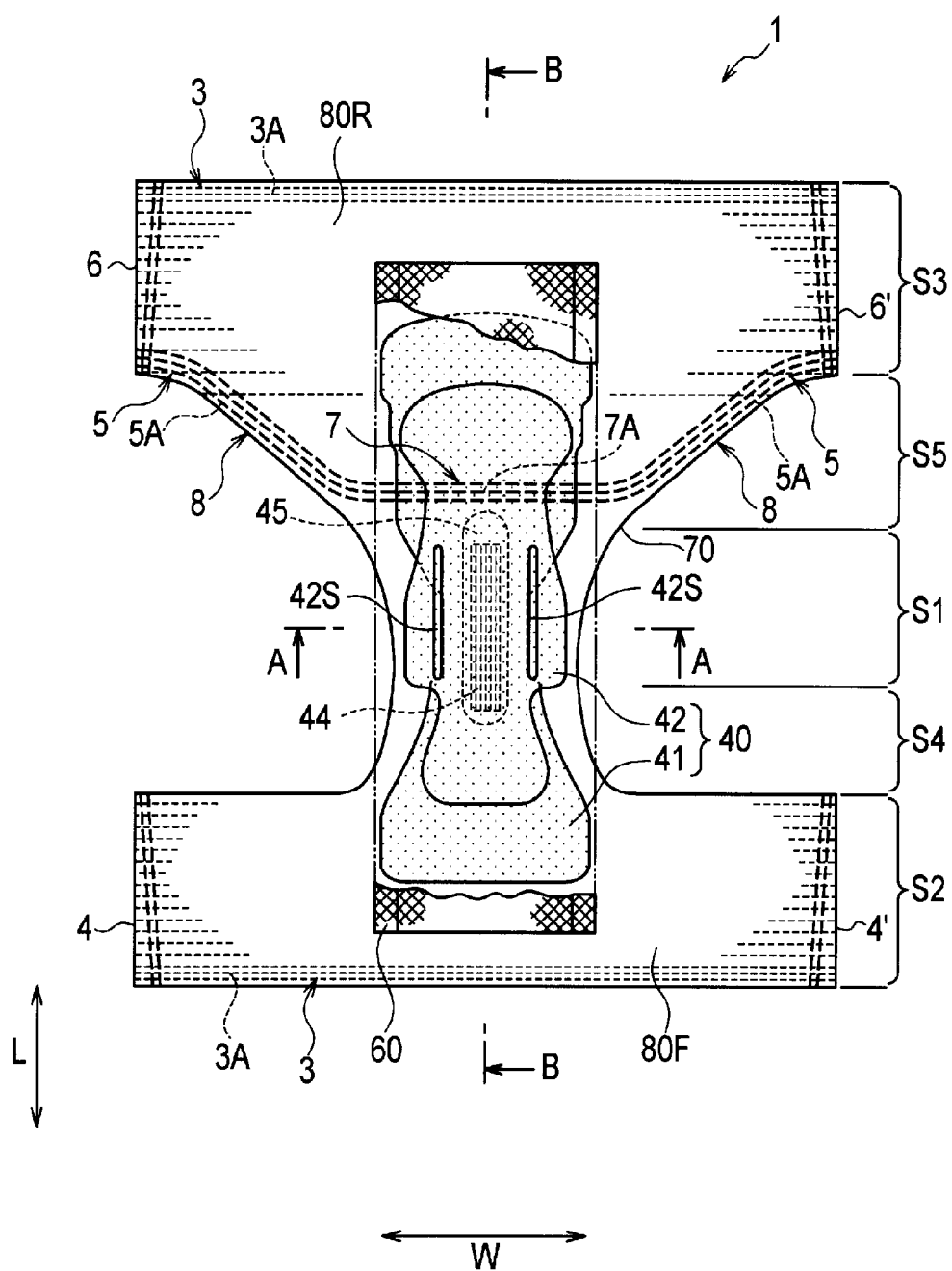
FIG. 2 is an exploded plan view of the diaper 1 according to the first embodiment.
Figure 3:
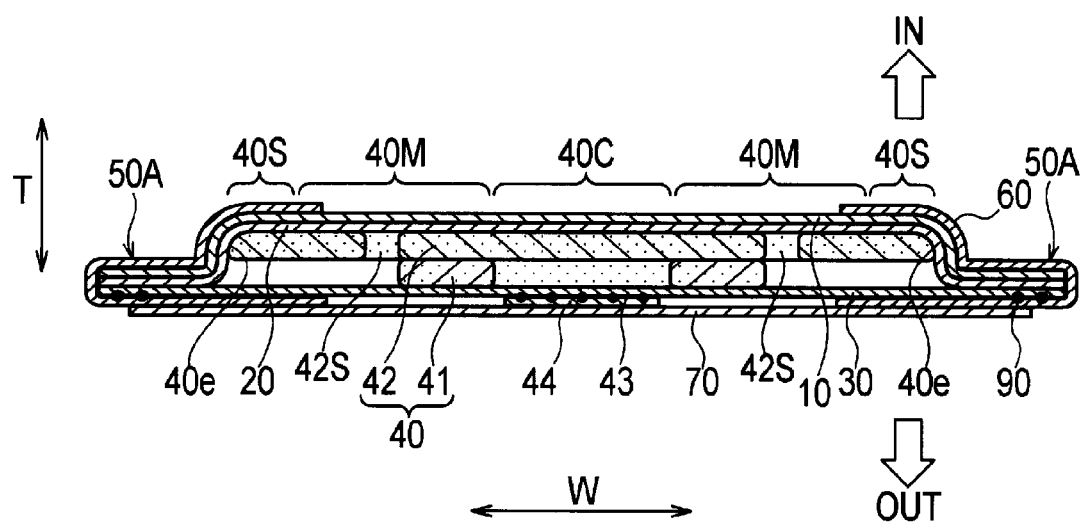
FIG. 3 is a widthwise sectional view of the diaper 1 taken along the line A-A shown in FIG. 2.
Figure 4:
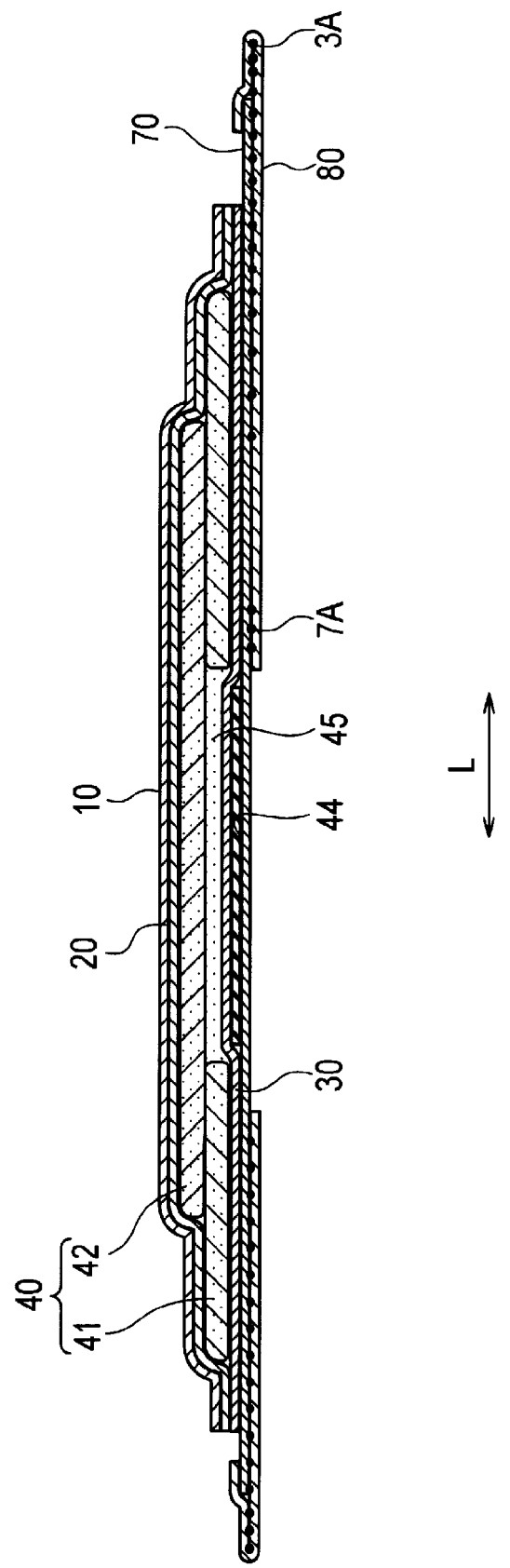
FIG. 4 is a lengthwise sectional view of the diaper 1 taken along the line B-B shown in FIG. 2.

FIG. 2 is an exploded plan view of the disposable diaper 1 according to the embodiment. FIG. 3 is a widthwise sectional view of the disposable diaper 1 taken along the line A-A shown in FIG. 2. FIG. 4 is a lengthwise sectional view of the disposable diaper 1 taken along the line B-B shown in FIG. 2.

As shown in FIG. 2 to FIG. 4, the disposable diaper 1 has: a front waistline region S2 which corresponds to a wearer's front waistline; and a back waistline region S3 which corresponds to the wearer's back waistline. The disposable diaper 1 also has a crotch portion region S1, a foreside middle inside leg region S4 and a backside middle inside leg region S5.

The crotch portion region S1 is a region applied to a wearer's crotch portion at which a width between both legs is the narrowest when the wearer closes his or her legs. The foreside middle inside leg region S4 is positioned between the crotch portion region S1 and the front waistline region S2 in a lengthwise direction L of an absorber 40. The backside middle inside leg region S5 is positioned between the crotch portion region S1 and the back waistline region S3 in the lengthwise direction L.

The front waistline side edge portion 4 is bonded with the back waistline edge portion 6 and the front waistline edge portion 4' is bonded with a back waistline edge portion 6', whereby the disposable diaper 1 is formed as a pant-type diaper.

A waist gather 3 is provided in the front waistline region S2 and the back waistline region S3. The waist gather 3 has an elongated waist elastic member 3A, such as a synthetic rubber, which is disposed so as to expand or shrink along a widthwise direction W of the absorber 40. The waist elastic member 3A is bonded with an exterior topsheet 70, a foreside exterior backsheet 80F and a backside exterior backsheet 80R by means of an adhesive (for example, a hot-melt adhesive) in a state in which the member is expanded along the widthwise direction W of the disposable diaper 1.

A leg gather 5 and an absorber crossing gather 7 are formed at the middle inside leg edge portion 8 of the backside exterior backsheet 80R. The leg gather 5 is formed so as to be taken along a wearer's leg portion. The absorber crossing gather 7 is formed so as to cross the absorber 40 along the widthwise direction W. The leg gather 5 and the absorbent crossing gather 7 integrally communicate with each other. The leg gather 5 has a plurality of leg elastic members 5A, and the absorber crossing gather 7 has a plurality of crossing elastic members 7A which communicate with the leg elastic members 5A.

The disposable diaper 1 is provided with a topsheet 10, an absorber 40, a side sheet 60, an exterior topsheet 70, a foreside exterior backsheet 80F, and a backside exterior backsheet 80R. The topsheet 10, the absorber 40, the side sheet 60, the exterior topsheet 70, and the foreside exterior backsheets 80F and 80R are bonded with each other by means of an adhesive or thermal fusion bonding or the like.

The topsheet 10 is a sheet forming a skin contact surface which can come into direct contact with the wearer's skin. The topsheet 10 is formed of a liquid-permeable sheet such as a hydrophilic nonwoven cloth or a woven cloth, an aperture plastic film, or an aperture hydrophilic nonwoven cloth.

An absorber topside covering sheet 20 is provided between the topsheet 10 and the absorber 40. The absorber topside covering sheet 20 is formed of a liquid-permeable sheet such as a hydrophilic nonwoven cloth or a woven cloth, an aperture plastic film, an aperture hydrophobic nonwoven cloth, or tissue.

An absorber backside covering sheet 30 is a provided at a non-skin contact surface side which is a surface opposite to a topsheet 10 or an absorber topside covering sheet 20 via an absorber 40. The absorber backside covering sheet 30 is formed of a sheet such as a liquid-impermeable film (polyethylene, for example). In FIG. 3, although not shown, at a portion at which side slits 42S are formed, the absorber topside covering sheet 20 is bonded with the absorber backside covering sheet 30 as described later.

The absorber 40 is covered with the absorber topside covering sheet 20 and the absorber backside covering sheet 30. The absorber 40 has: a lengthwise direction L which is oriented from the front waistline region S2 to the back waistline region S3; and a widthwise direction which is orthogonal to the lengthwise direction L. Further, the absorber 40 has: an inward direction IN which is oriented to a wearer wearing the disposable diaper 1 and an outward direction OUT which is oriented to be opposite to the inward direction.

At a side edge portion 50A at which the absorber topside covering sheet 20 and the absorber backside covering sheet 30 overlap each other at the outside of the widthwise direction W of the absorber 40, a side elastic member 90 is provided in a state in which the member expands along the lengthwise direction L. The side elastic member 90 is continuous from the foreside middle inside leg region S4 to the backside middle inside leg region S5 through the crotch portion region S1. The side elastic member is provided between the absorber backside covering sheet 30 and a side sheet 60. The side elastic member 90 is formed of a synthetic rubber having elasticity.

The side sheet 60 is provided so as to integrally cover the topsheet 10, the absorber topside covering sheet 20, and the absorber backside covering sheet 30 at both side edges in the widthwise direction W of the absorber 40. The side sheet 60 is formed of a sheet such as a liquid-impermeable nonwoven cloth, and a leakage-preventing wall for preventing side leakage of bodily waste is comprised of the side sheet 60 and the side elastic member 90.

The exterior topsheet 70 is formed from the front waistline region S2 to the back waistline region S3 through the foreside middle inside leg region S4, the crotch portion region S1, and the backside middle inside leg region S5. The exterior topsheet 70 is formed so that its width in the widthwise direction W is greater in the front waistline region S2 and the back waistline region S3 than in any other region. The exterior topsheet 70 can be formed of an air-through nonwoven cloth, a spunbond nonwoven cloth, an SMS nonwoven cloth, or a water-resistive film or the like.

The foreside exterior backsheet 80F is provided at a non-skin contact surface side more than the exterior topsheet 70 in the front waistline region S2. The backside exterior backsheet 80R is provided at the non-skin contact surface side more than the exterior topsheet 70 in the back waistline region S3. One end of the foreside exterior topsheet 80F in the lengthwise direction L and one side of the backside exterior backsheet 80R in the lengthwise direction is folded back to the skin contact surface side, so as to envelope the end parts in the lengthwise direction L of the exterior topsheet 70. The foreside exterior backsheet 80F can be formed of an air-through nonwoven cloth, a spunbond nonwoven cloth, an SMS nonwoven cloth, or a water-resistive film or the like.

A central elastic member 44 is provided along a lengthwise direction L, and is provided at a position which is superimposed with a central aperture 45 in a thickness direction T of the disposable diaper 1. The central elastic member 44 is formed to be convex in an inward direction IN, namely, to be superimposed with the absorber 40 in a lengthwise direction L so that the absorber 40 can be curved to be convex toward a wearer. In the embodiment, the central elastic member 44 comprises the central curving portion.

The central elastic member 44 is provided on a non-skin contact surface side of the absorber. Specifically, it is provided on an outer face of the backside covering sheet 30. Further, an elastic member covering sheet 43 is provided at a non-skin contact surface side of the central elastic member 44, and the central elastic member 44 is bonded between the absorber backside covering sheet 30 and the elastic member covering sheet 43 by means of an adhesive. The central elastic member 44 may be bonded with a topsheet 10 or may be bonded with an exterior topsheet 70.

A material for the central elastic member includes, for example, a synthetic rubber such as styrene-butadiene, butadiene, isoprene, or neoprene, a natural rubber, EVA, elastic polyolefin, spandex, or foamed polyurethane or the like. As another material for the central elastic member 44, an elastic sheet such as an elastic nonwoven cloth may be employed. In the first embodiment, the central elastic member 44 is disposed in a state in which seven members are preferably arranged over about 30 mm in the widthwise direction W. A length in the lengthwise direction of the central elastic member 44 is preferably about 180 mm. A material for the central elastic member 44 is spandex, and is elastically fixed in thickness of 620 dtex and at an expansion magnification of 1.8 times. As will be readily appreciated by those skilled in the art, however, the central elastic member is not limited to these arrangements and may take other forms, such as but not limited to an elastic belt-like member.

Materials described in Japanese Patent Application Laid-open No. 2006-346439, for example, may be employed for constituent elements configuring the above-described disposable diaper 1.

(2) Structure of an Absorber

Figure 5:
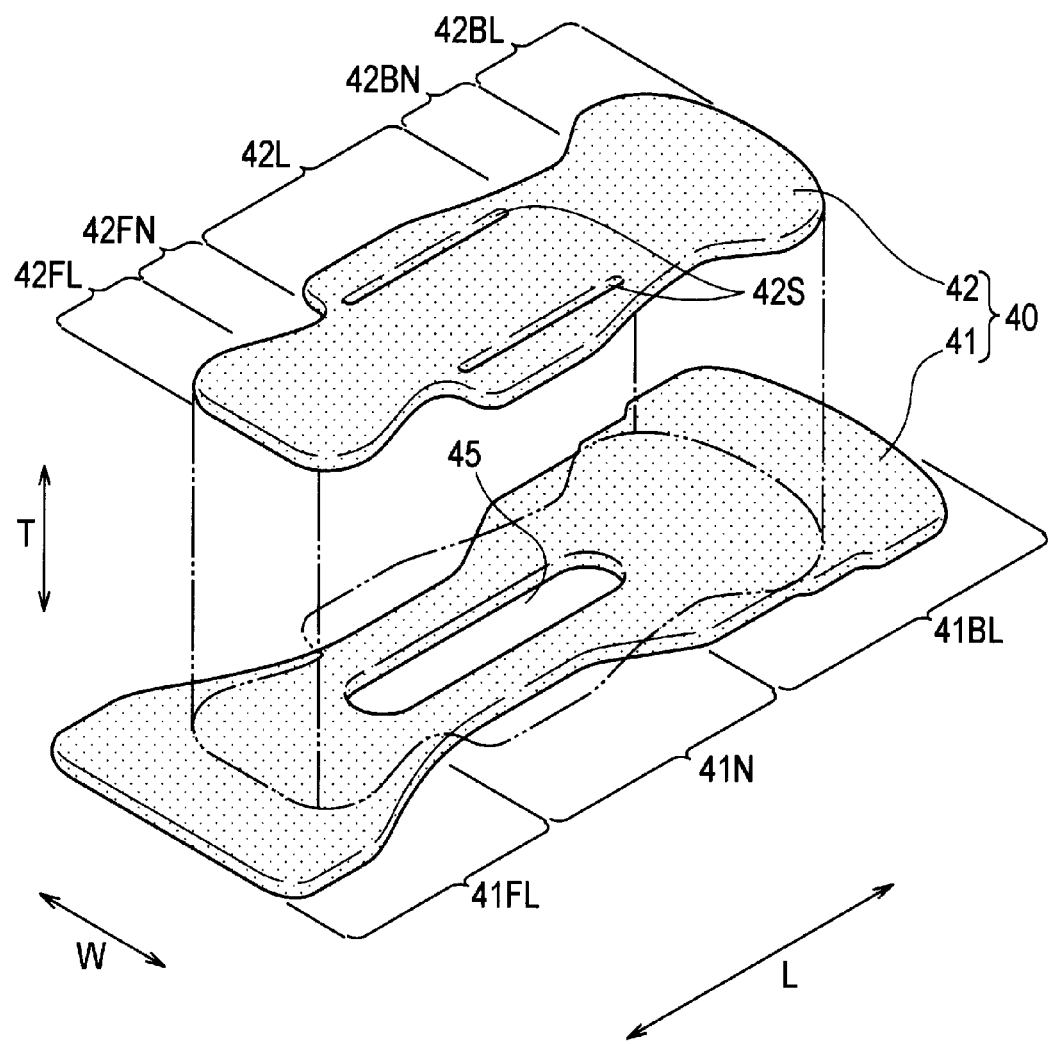
FIG. 5 is a perspective view of an absorber 40 according to the first embodiment.

FIG. 5 is a perspective view of an absorber 40. As shown in FIG. 5, the absorber 40 has a first layer 41 and a second layer 42 which is superimposed on the first layer 41. The first layer 41 is positioned at a wearer's non-skin contact surface side, and the second layer 42 is positioned at the wearer's skin contact surface side.

The first layer 41 and the second layer 42 are preferably composed of a cotton-like pulp and a highly polymerized absorbent polymer (SAP). The first layer 41 may be formed in a state in which it is mixed with pulp of 300 g/m$^2$ and SAP of 150 g/m$^2$, and the thickness in the thickness direction T is preferably about 3.0 mm. The second layer 42 may be formed in a state in which it is mixed with pulp of 200 g/m$^2$ and SAP of 90 g/m$^2$, and the thickness in the thickness direction T is preferably about 2.0 mm. Namely, a thickness of a portion at which the first layer 41 and the second layer 42 are superimposed on each other is preferably about 5.0 mm.

As shown in FIG. 2 and FIG. 5, the first layer 41 has: a narrow portion 41N which is concave toward a center of the first layer in the widthwise direction W and has a predetermined width in the widthwise direction W; and a wide portion 41FL and a wide portion 41BL which are formed at both ends of the narrow portion 41N in the lengthwise direction L. The narrow portion 41N is formed in a crotch portion region S1. In addition, the wide portion 41FL is formed in a front waistline region S2, and the wide portion 41BL is formed in a back waistline region S3. A side edge of the narrow portion 41N, a side edge of the wide portion 41FL, and a side edge of the wide portion 41BL are continuous with one another and are connected by means of a curved line, and the first layer 41 has an hourglass-type planar shape.

In addition, in the first layer 41, a central aperture 45 is formed at a central part of the widthwise direction W. The central aperture 45 has a longitudinally elongated shape extending along the lengthwise direction L, and is formed across a crotch portion region S1, a foreside middle crotch region S4, and a backside middle crotch region S5. In particular, the central aperture 45 is formed so as to extend a distance into the foreside middle crotch region S4. Preferably, the central aperture extends a greater distance into the foreside middle crotch region than into the backside middle crotch region. A length of the central aperture 45 is preferably about 200 mm and a width thereof is preferably about 40 mm.

The second layer 42 has an overhang portion 42L which overhangs to the outside in the widthwise direction W more than the narrow portion 41N of the first layer 41. A position in the lengthwise direction L of the overhang portion 42L is superimposed on that in the lengthwise direction L of the narrow portion 41N.

A narrowed portion 42FN and a narrowed portion 42BN which are convex toward a center of the widthwise direction W are formed at side edges of the second layer 42. The narrowed portions 42FN, 42BN are positioned at the outside of the crotch portion region S1 in the lengthwise direction L.

In addition, wide portions 42FL, 42BL which are wider than the narrowed portions 42FN, 42BN are formed at the outside in the lengthwise direction L of the constricted portions 42FN, 42BN. In the embodiment, the rigidity of the wide portion 42FL and the wide portion 42BL is adapted so as to be identical to or higher than that of the overhang portion 42L.

In addition, a pair of side slits 42S are formed in the second layer 42. The side slits 42S are formed in the absorber 40 along the lengthwise direction L so as to be convex in the outer direction OUT, namely so that the absorber 40 can be curved to be convex at the opposite side to the central aperture 45. A length of the side slits 42S is preferably smaller than that of the central aperture 45, and a width of the side slits 42S is preferably smaller than that of the central aperture 42S. Specifically, the length of the side slit 42S is preferably about 120 mm and the width thereof is preferably about 10 mm. It is preferable that the width of the side slit 42S is 5 mm to 12 mm.

The absorber 49 comprised of such first layer 41 and second layer 42, as shown in FIG. 3, has a central portion 40C, a middle portion 40M, and a side edge portion 40S. The central portion 40C is formed at a center part of the absorber 40 in the widthwise direction W. The middle portion 40M is positioned between the central portion 40c and the side edge portion 40S. The side edge portion 40S is formed at a side edge 40e of the absorber 40 in the widthwise direction W.

In the embodiment, the central portion 40C and the side edge portion 40S are formed of only the second layer 42. On the other hand, the middle portion 40M is formed of the first layer 41 and the second layer 42, except for in the portion outside of the side slit 42S in the widthwise direction. Therefore, a thickness of the central portion 40C and the side edge portion 40S is about 2.0 mm, and a thickness of the middle portion 40 is about 5.0 mm. Namely, the thickness of the absorber 40 in the central portion 40C and the side edge portion 40S may be smaller than that of the absorber 40 at the middle portion 40M. As shown in FIG. 3, at the middle portion 40M, a partial region (inside of the side slit 42S in the widthwise direction) may be thicker than the central portion 40C and the side edge portion 40S. In an alternative arrangement, at the middle portion 40M, an outside portion in the widthwise direction W may be thickened instead of the inside portion, as described.

The thickness of the absorber 40 is measured by sandwiching a desired portion between measuring portions of a thickness measuring instrument in a state in which the absorber is expanded in product length and product width (namely, in a flat state such that no wrinkle occurs). As an available measuring instrument, for example, PEACOCK-manufactured thickness gauge (measuring portions: 5 mm in diameter, measuring pressure: 163 g/cm$^2$) can be employed.

In the embodiment, the first layer 41 and the second layer 42 are integrated with each other by being compressed along the thickness direction T. The first layer 41 and the second layer 42 may be integrated with each other by means of an adhesive or thermal bonding or the like. In addition, while in the absorber 40, the first layer 41 is positioned at the non-contact surface side and the second layer 42 is positioned at the skin contact surface side, the second layer 42 may be positioned at the non-contact surfaces side and the first layer 41 may be positioned at the skin contact surface side.

(3) Shape Change of an Absorber

Figure 6:
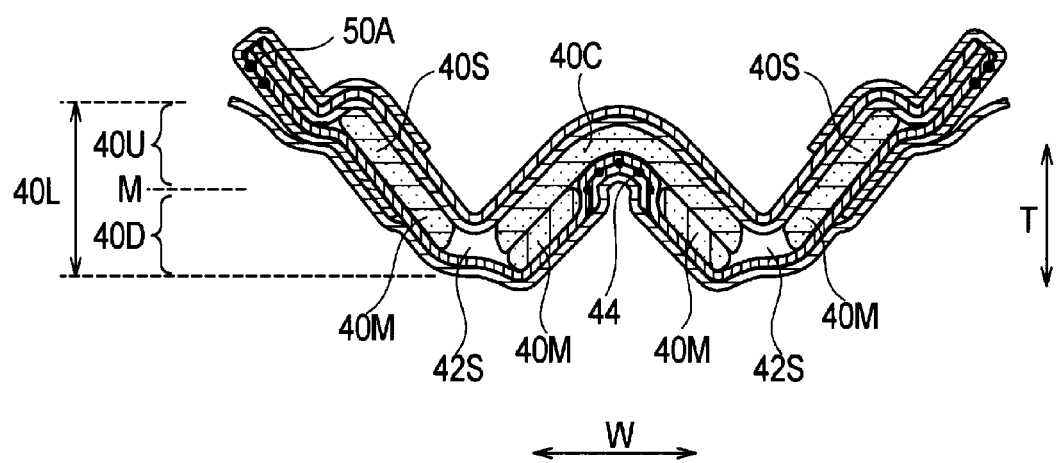
FIG. 6 is a sectional view schematically showing a wearing state of the disposable diaper 1 according to the first embodiment.

FIG. 6 is a sectional view (which is taken along the line A-A of FIG. 2) schematically showing a wearing state of a disposable diaper 1. As shown in FIG. 6, when the disposable diaper 1 is worn, the absorber 40 is curved with respect to a central elastic member 44 and a side slit 42S and then a sectional shape which is taken along a widthwise direction W of the disposable diaper 1 is formed in a W-letter shape. As a result, a top side of the absorber 40 formed to be convex in an inward direction IN by means of a central elastic member 44 comes into contact with a wearer's crotch portion. In addition, a central portion 40C and a side edge portion 40S are positioned in an upper region 40U which is proximal to a wearer's body more than an imaginary line M which is obtained by dividing a height 40L of the deformed absorber 40 into two sections. On the other hand, a middle portion 40M is positioned in a lower region 40D which is distant from the wearer's body more than the imaginary line M. Namely, the central portion 40C and the lower region 40D which are small in thickness are positioned at the wearer's skin side and the middle portion 40M which is large in thickness is spaced from the wearer's skin. It is preferable that a side edge portion (leg standing gather) including the side elastic member 90 is positioned at a position which is higher than the central portion 40C, namely at the wearer's side in the thickness direction T in the figure.

Figure 7:
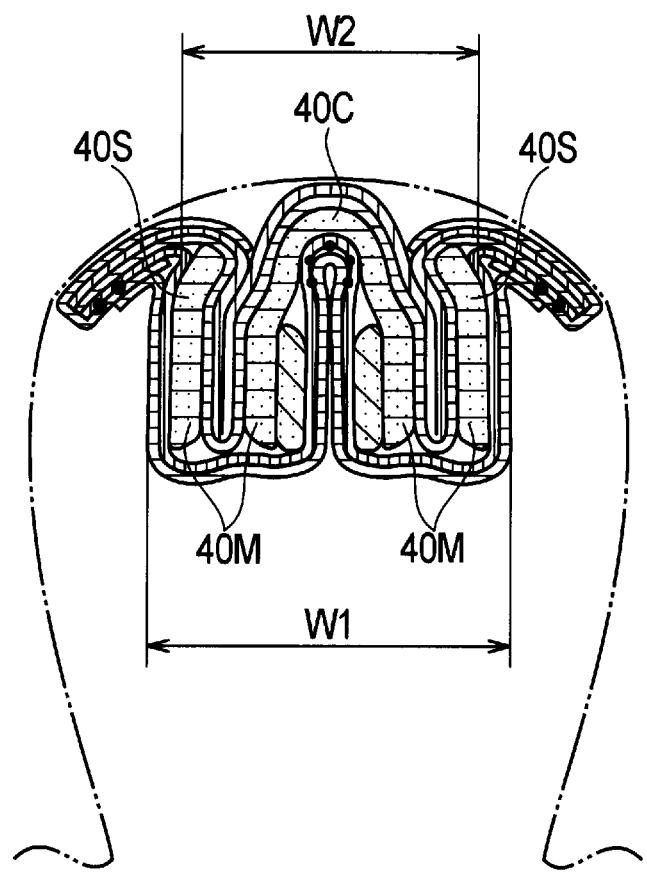
FIG. 7 is a sectional view schematically showing a wearing state (at the time of closing legs) of the disposable diaper 1 according to the first embodiment.

FIG. 7 is a sectional view (which is taken along the line A-A of FIG. 2) schematically showing a wearing state of the disposable diaper 1 in a case where a wearer closes his or her legs. The imaginary line in the figure indicates the wearer's crotch portion and both leg portions.

As shown in FIG. 7, when the wearer closes his or her legs the sectional shape of the disposable diaper 1 varies from the state shown in FIG. 6 to the state shown in FIG. 7. As shown in FIG. 7, in a case where the wearer closes both legs, the central portion 40C and the side edge portion 40S are positioned so as to come into contact with the wearer's crotch portion. On the other hand, the middle portion 40M is positioned more downward (at the crotch side) than the central portion 40C and the side edge portion 40S. Namely, a width W2 of the disposable diaper 1 at a position including the central portion 40M and the side edge portion 40S is smaller than a width W1 of the disposable diaper 1 at a position including the middle portion 40M. Thus, the sectional shape of the disposable diaper 1 is formed in a tapered shape such that the diaper narrows from the inside leg to the crotch portion.

The position of the width W2 is a thickness of the absorber 40 at a position lowered by a distance of ⅓ of the upper region 40U from an upper end of the upper region 40U in the thickness direction T. In addition, the width W1 is a thickness of the absorber 40 at a position rising by a distance of ⅓ of the lower region 40D from a lower end of the lower region 40D in the thickness direction.

The disposable diaper 1 described above is provided with: a central elastic member 44 which is formed at the absorber 40 so that the absorber 40 can be curved to be convex in the inward direction IN; and a pair of side slits 42S which are formed at the absorber 40 so that the absorber 40 can be curved to be convex in the outward direction OUT. Thus, at the time of wearing the disposable diaper 1, the central portion 40C that is formed in convex toward the wearer's excretion portion easily comes into intimate contact with the excretion portion. In addition, the middle portion 40M forms a concave portion, so that bodily waste easily enters the concave portion and direct contact between the wearer's skin and the bodily waste can be restrained.

In particular, a central aperture 45 is formed at a portion of the central elastic member 44. In addition, since side slits 42S are formed at the absorber 40, even in a case where the absorber 40 absorbs liquid and swells, the absorber 40 is easily curved in comparison with a case in which a thin portion is formed at the absorber 40 to form a curve forming portion. In addition, the sectional shape of the disposable diaper 1 is formed in a tapered shape such that the diaper narrows from the inside leg to the crotch portion, and the diaper is easily accommodated in a gap of the wearer's crotch portion, causing the wearer to hardly have an uncomfortable feeling.

Further, a thickness of the absorber 40 at the central portion 40C and the side edge portion 40S is smaller than that of the absorber 40 at the middle portion 40M. Thus, the central portion 40C easily come into contact with the wearer's excretion portion, bodily waste from the excretion portion can be readily absorbed and the bodily waste going along the skin can be restrained. In addition, since the thickness of the absorber 50 at the central portion 40C and the side edge portion 40S that are proximal to the wearer's skin is restrained, even if the wearer closes his or her legs, the wearer hardly has an uncomfortable feeling. Moreover, at the middle portion 40M, since the thickness of the absorber 40 is large, absorptive power of liquid or the like is improved.

That is, according to the disposable diaper 1, absorptive power can be improved while an uncomfortable feeling due to the thickness of an absorber is reduced in a case where the absorber is curved to thereby improve a wearer's feeling of wearing or to prevent leakage of bodily waste.

In the embodiment, the absorber 40 is a two-layered structure of the first layer 41 and the second layer 42. Thus, an absorber of which thickness is different depending on the central portion 40C, the middle portion 40M, and the side edge portion 40S can be easily manufactured.

In the embodiment, a position in the lengthwise direction L of the overhang portion 42L of the second layer 42 is superimposed on that of the lengthwise direction L of the narrow portion 41N of the first layer 41. Thus, the absorber 40 is easily curved with respect to the side slit 42S.

In the embodiment, narrowed portions 42FN, 42BN of the second layer 42 are positioned at the outside of the crotch portion region S1 in the lengthwise direction L. Thus, an overhang portion 42L that is formed in the crotch portion region S1 is easily deformed toward the wearer's side.

In the embodiment, rigidity of the wide portion 42 FL and the wide portion 42BL is adapted so as to be identical to or higher than that of the overhang portion 42L. Thus, even in a case where the absorber 40 has been deformed in the W-letter shape, a portion of the wide portion 42FL and the wide portion 42BL is hardly affected by the deformation in the W-latter shape. Namely, the width of the wide portion 42FL and the wide portion 42BL can be restrained from being narrowed due to the deformation. Therefore, an absorption area of the absorber 40 is allocated and absorptive power can be further enhanced.

In the embodiment, the absorber topside covering sheet 20 is bonded with the absorber backside covering sheet 30 at a portion at which the side slits 42S are formed. Thus, the absorber 40 can be restrained from being deformed to thereby close the side slits 42S, or alternatively, the absorber 40 can be restrained from being twisted from the side slits 42S. In addition, even in a case where the absorber 40 absorbs liquid and swells, since the side slits 42S can be prevented from being closed, a slit portion easily functions as a curve forming portion reliably.

Second Embodiment

Next, a configuration of a disposable diaper 1X according to a second embodiment will be described with reference to the drawings. The same constituent elements of the disposable diaper 1 according to the first embodiment described above are designated by the same reference numerals, and matters different therefrom is mainly explained.

Figure 8:
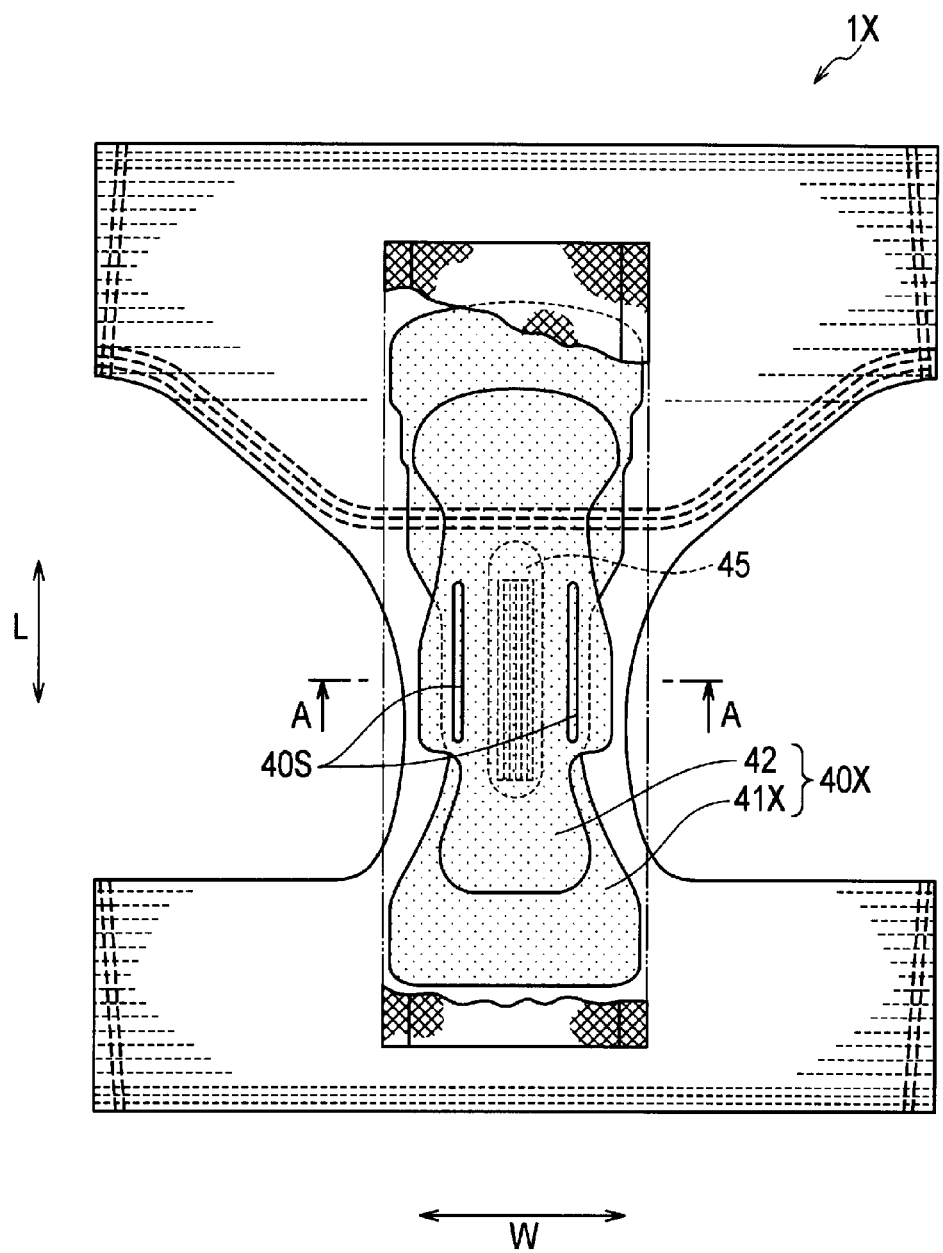
FIG. 8 is an exploded plan view of a disposable diaper 1X according to a second embodiment.
Figure 9:
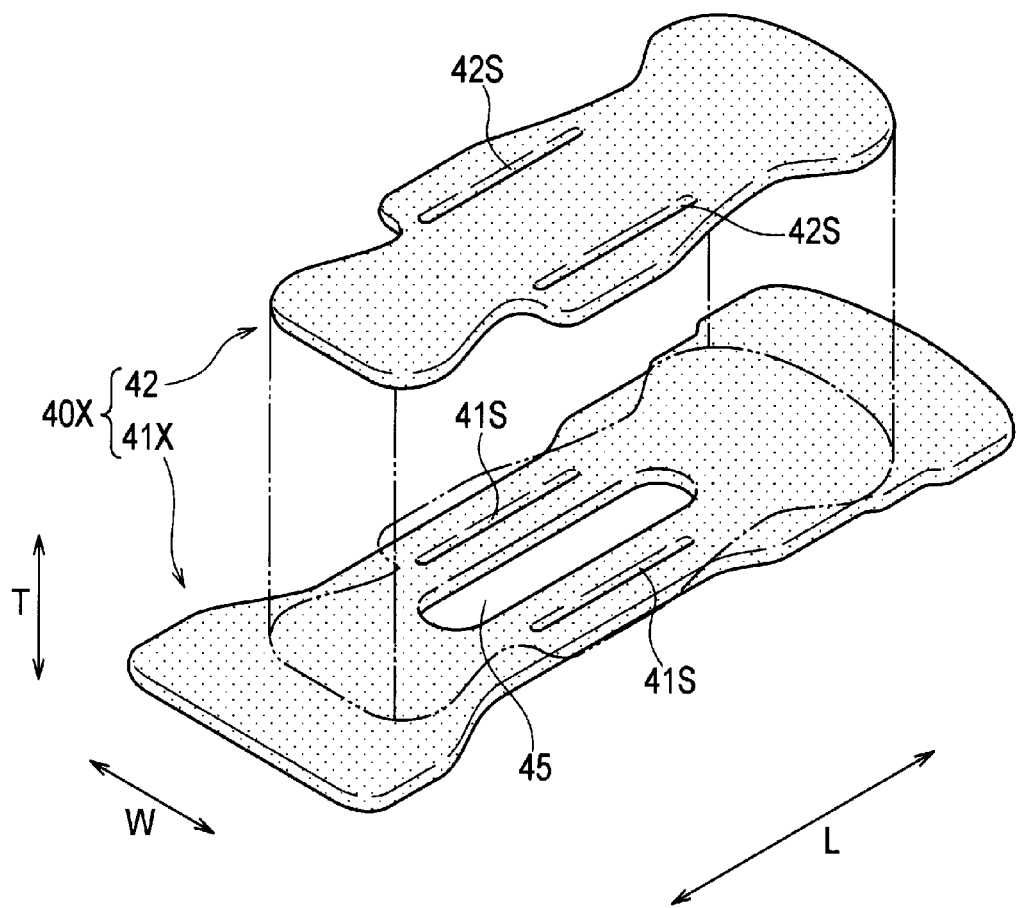
FIG. 9 is a perspective view of an absorber 40X according to the second embodiment.
Figure 10:
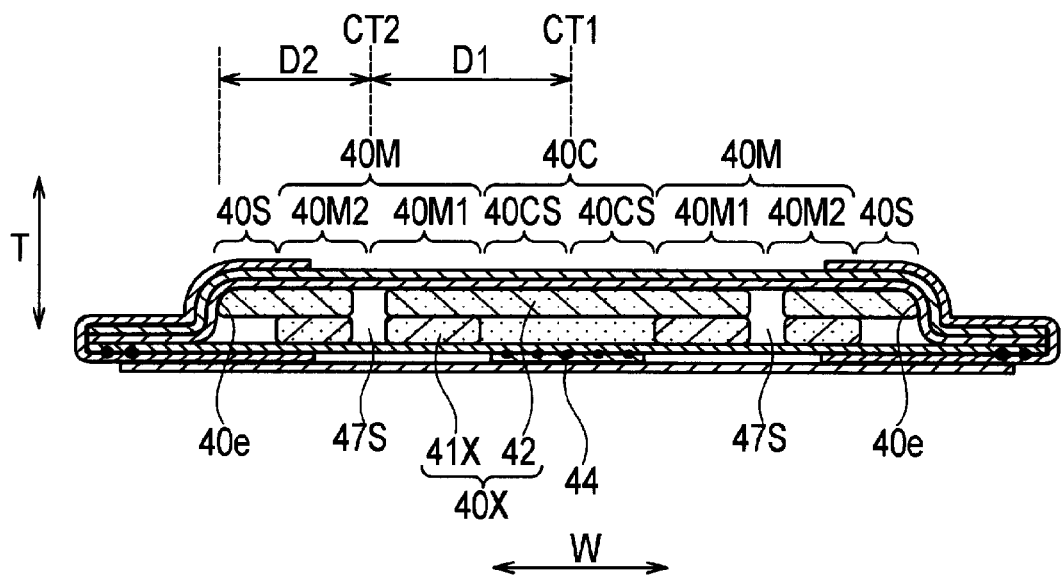
FIG. 10 is a widthwise-sectional view of the disposable diaper 1X taken along the line A-A shown in FIG. 8.

FIG. 8 is an exploded plan view of the disposable diaper 1X, incorporating an absorber 40X according to the second embodiment. FIG. 9 is a perspective view of the absorber 40X according to the second embodiment. FIG. 10 is a widthwise sectional view of the disposable diaper 1X that is taken along the line A-A shown in FIG. 8.

As shown in FIG. 8 to FIG. 10, in the disposable diaper 1X, a structure of the absorber 40X is different from that of the absorber 40 according to the first embodiment. Specifically, a structure of a first later 41X is different from that of the first layer 41. Other constituent elements are identical to those of the disposable diaper 1.

In the first layer 41X, a pair of side slits 41S is provided, with a slit either side of a central aperture 45. The side slits 41S are formed along a lengthwise direction L and are formed at positions superimposed on the side slits 42S. Namely, the side slits 41S and the side slits 42S are superimposed on each other, whereby side slits 47S are formed.

In addition, a width of the first layer 41X at a portion at which the side slit 41S and the central aperture 45 are formed is larger than that of the first layer 41 according to the first embodiment.

As shown in FIG. 10, in the embodiment, a central portion 40C includes a sub-central portion 40CS which is a region from a boundary associated with a middle portion 40M to a center CT1 of a central elastic member 44, in a widthwise direction W. In addition, the middle portion 40M includes, in the widthwise direction W, an inside middle portion 40M1 which is a region from a side slit 47S to a boundary associated with the central portion 40C; and an outside middle portion 40M2 which is a region from the side slit 47S to a boundary associated with a side edge portion 40S.

A thickness of the absorber 40X at the sub-central portion 40CS is smaller than that of the absorber 40X at an inside middle portion 40M1. In addition, a thickness of the absorber 40X at a side edge portion 40S is smaller than that of the absorber 40X at the outside middle portion 40M2. Namely, the thickness of the absorber 40X at the central portion 40C and the side edge portion 40S is smaller than that of the absorber 40X at the middle portion 40M.

Further, in the embodiment, the middle portion 40M is formed from a position corresponding to about half of a distance D1 between a center CT1 of the central elastic member 44 and a center CT2 of the side slit 47S in a widthwise direction W to a position corresponding to about half of a distance D2 between a center CT2 of the side slit 47S and a side edge 40e. In addition, in the widthwise direction, a width of the sub-central portion 40CS is substantially identical to that of the side edge portion 40S.

Figure 11:
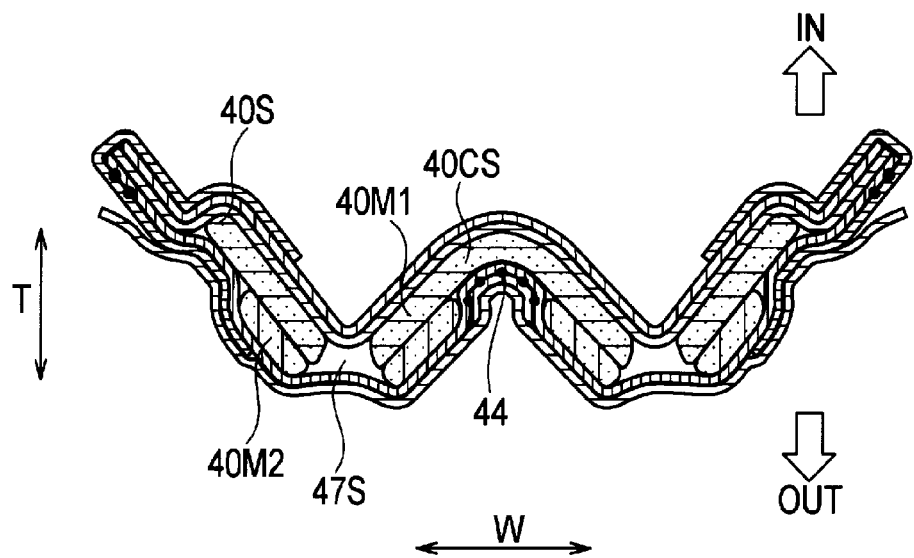
FIG. 11 is a sectional view schematically showing a wearing state of the disposable diaper 1X according to the second embodiment.
Figure 12:
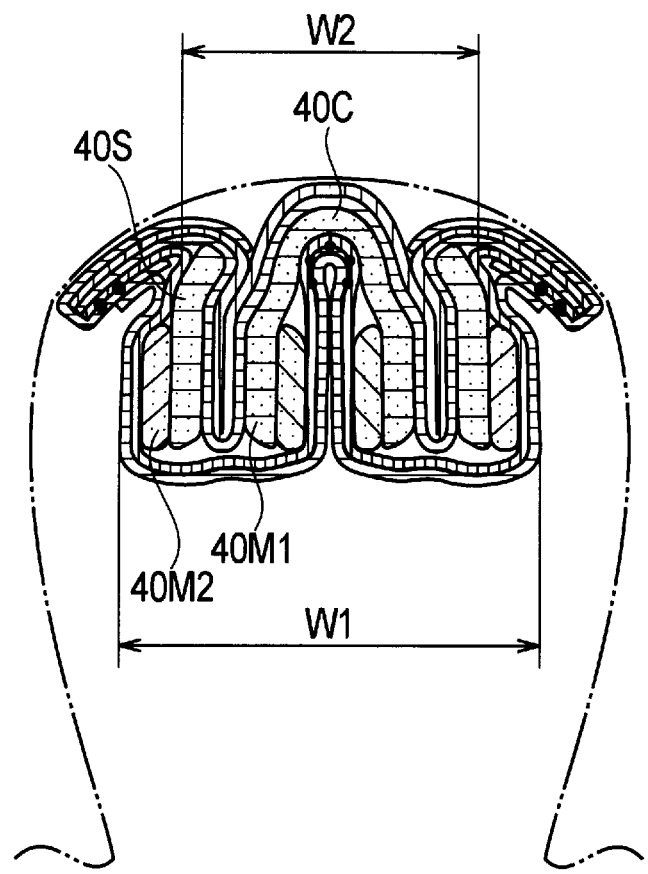
FIG. 12 is a sectional view (at the time of closing legs) schematically showing a wearing state of the disposable diaper 1X according to the second embodiment.

FIG. 11 is a sectional view schematically showing a wearing state of the disposable diaper 1X. In addition, FIG. 12 is a sectional view (which is taken along the line A-A of FIG. 8) schematically showing a wearing state of the disposable diaper 1X in a case where a wearer closes his or her legs. In FIG. 11 and FIG. 12, only left-side portions with respect to a center of the widthwise direction are designated by reference numerals.

As shown in FIG. 11, in the disposable diaper 1X according to the embodiment as well, the absorber 40X is curved with respect to the central elastic member 44 and the side slit 47S, and the sectional shape taken along the widthwise direction W of the disposable diaper 1X is deformed in the W-letter shape. In addition, as shown in FIG. 12, when a wearer closes his or her legs, the sectional shape of the disposable diaper 1X is formed in a tapered shape such that the diaper narrows from the inside leg to the crotch portion.

In particular, in the embodiment, an outside middle portion 40M2 is formed at the outside of the side slit as well, so that the width W1 of the disposable diaper 1 at a position including the middle portion 40M is larger than the width W1 of the disposable diaper 1 according to the first embodiment. Namely, in the disposable diameter 1X, a difference between the width W1 and the width W2 increases, and the sectional shape of the disposable diaper 1X is formed in a further tapered shape from the inside leg to the crotch portion.

Thus, according to the disposable diaper 1X, absorptive force can be further improved while an uncomfortable feeling due to the thickness of the absorber is reduced.

Third Embodiment

Next, a configuration of an absorber according to a third embodiment will be described with reference to the drawings. Same constituent elements of the absorber according to the first embodiment described above are designated by same reference numerals, and only matters different therefrom will be mainly explained.

Figure 13:
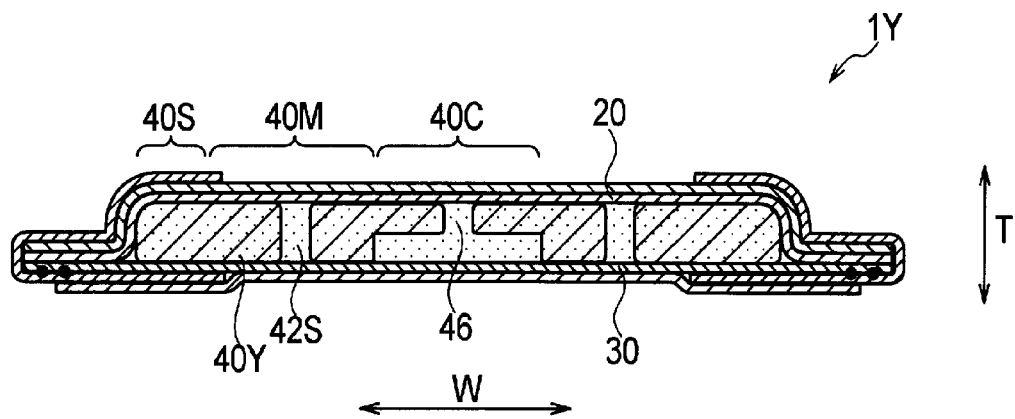
FIG. 13 is a widthwise-sectional view of a disposable diaper 1Y according to a third embodiment.
Figure 14:
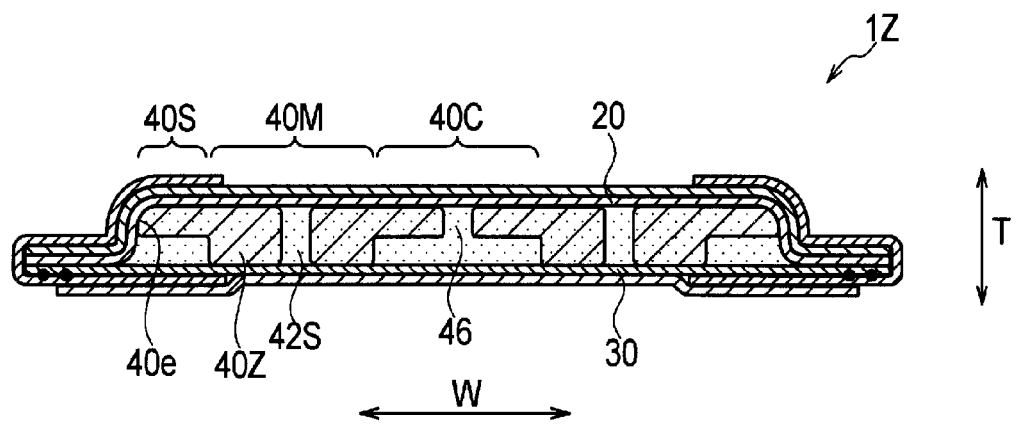
FIG. 14 is a widthwise sectional view of a disposable diaper 1Z according to a modification of the third embodiment.

FIG. 13 is a widthwise sectional view of a disposable diaper 1Y, including an absorber, according to the embodiment. FIG. 14 is also a widthwise sectional view of a disposable diaper 1Z, including an absorber, according to the embodiment. FIG. 13 and FIG. 14 show widthwise sectional views of the disposable diapers, which are taken along the line A-A of FIG. 2. In FIG. 13 and FIG. 14, only left-side portions with respect to a center of a widthwise direction W, are designated by reference numerals.

An absorber 40Y of the disposable diaper 1Y and an absorber 40Z of the disposable diaper 1Z are a one-layer structure instead of a two-layered structure. In addition, at the absorber 40Y and the absorber 40Z, a central slit 46 is formed at the center of the widthwise direction in place of a central elastic member 44.

The absorber 40Y and the absorber 40Z are different from each other in thickness of a side edge portion 40S. Specifically, at the absorber 40Y, the thickness of the side edge portion 40S is substantially identical to that of a middle portion 40M. Namely, the thickness of the absorber 40Y at a central portion 40C is smaller than that of the absorber 40Y at the middle portion 40M, whereas the thickness of the side edge portion 40S is substantially identical to that of the middle portion 40M.

On the other hand, at the absorber 40Z, the thickness of a side edge portion 40S is smaller than that of a middle portion 40M. The side edge portion 40S may be gradually smaller in thickness, as the absorber goes from a side slit 42S to a side edge 40E. In addition, the thickness of the absorber 40Z may be gradually smaller in thickness, as the absorber goes from a side slit 42S to the center of the widthwise direction W.

In addition, in order to integrally form the absorber 40Y or the absorber 40Z of which thickness is different in the different portions, for example, a material for the absorbers is filled and laminated in a molding die having different depths of grooves having the shape of the absorbers and then press processing is applied, whereby these absorbers can be produced. Moreover, a absorber topside covering sheet 20 may be bonded with a absorber backside covering sheet 30 at a portion at which the side slit 42S and the central slit 46 are formed.

Other Embodiments

As described above, while the contents of the present invention were disclosed through the embodiments of the present invention, it should not be understood that the statements and drawings forming part of this disclosure limits the present invention. From this disclosure, a variety of alternate embodiments, examples, and operational techniques are self-evident to one skilled in the art.

For example, while the absorber of the above-described embodiments has been described in combination with a pant-type disposable diaper, the absorber of the present invention may be applied to numerous other absorbent wearing articles, including but not limited to an open-type disposable diaper or a sanitary napkin.

While, in the above-described embodiments, a central curve forming portion was formed by employing slits or an elastic member, this portion may be formed in these or other embodiments by reducing the thickness of the absorber or applying emboss processing to the absorber.

Of course, the present invention includes a variety of embodiments which are not described herein. Therefore, a technical scope of the present invention is defined merely by specific matters of the invention according to a scope of claims which is reasonable from the above description.

The first aspects of the present invention described above may be arranged in at least the following items:

An absorber having: a lengthwise direction; a widthwise direction which is orthogonal to the lengthwise direction; an inward direction which is oriented to a wearer; and an outer direction which is oriented to a side opposite to the inward direction, wherein: the absorber has, in a crotch portion region applied to a crotch portion of the wearer, a central portion which is formed at a central part of the absorber in the widthwise direction, a pair of side edge portions including a side edge of the absorber in the widthwise direction, and a pair of middle portions which are positioned between the central portion and the side edge portions; at the central portion, a central curve forming portion is formed along the lengthwise direction so that the absorber can be curved to be convex in the inward direction; at the middle portion, a pair of side curve forming portions are formed along the lengthwise direction so that the absorber can be curved to be convex in the outer direction; a top face of the absorber, which is formed to be convex in the inward direction by the central curve forming portion, is adapted to come into contact with the crotch portion, and a thickness of the absorber at the central portion is smaller than a thickness of the absorber at the middle portion.

A disposable wearing article comprising an absorber according to the preceding item or any of the foregoing items.

Additionally, one or more of the following embodiments are provided in accordance with further aspects:

Preferably, a thickness of the absorber at the central portion and at the side edge portion is smaller than a thickness of the absorber at the middle portion.

Preferably, in the width direction, the middle portion includes an inside middle portion which is a region from the side curve forming portion to a boundary associated with the central portion; the central portion includes a sub-central portion which is a region from a boundary associated with the middle portion to the central curve forming portion in the widthwise direction; and a thickness of the absorber at the sub-central portion is smaller than a thickness of the absorber at the inside middle portion.

Preferably, the middle portion includes an outside middle portion which is a region from the side curve forming portion to a boundary associated with the side edge portion in the widthwise direction; and a thickness of the absorber at the side edge portion is smaller than a thickness of the absorber at the outside middle portion. Alternatively, the thickness of the absorber at the outside middle portion may be the same as the side edge portion, wherein the side edge portion may have the same thickness as the central portion or the same thickness as the inside middle portion, which has a greater thickness than the central portion.

Preferably, the middle portion is formed, in the widthwise direction, from a position corresponding to half of a distance between a center of the central curve forming portion and a center of the side curve forming portion, to a position corresponding to half of a distance between the center of the side curve forming portion and a side edge of the absorber.

Preferably, a width of the sub-central portion is identical to a width of the side edge portion in the widthwise direction.

Preferably, the absorber has a first layer and a second layer which is superimposed on the first layer; the central portion and the side edge portions are formed of only the second layer; and the middle portion is formed of the first layer and the second layer.

Alternatively, the central portion may be formed of only the second layer; with the middle portion and the side edge portion formed of the first layer and the second layer.

In either case, the middle portion may comprise the inside middle portion and the outside middle portion, and the outside middle portion may be formed of the second layer only or both the first and second layers.

Preferably, the average total weight of a water absorbent polymer in the first layer is greater than the average total weight of the water absorbent polymer in the second layer. Preferably, the first layer is thicker than the second layer.

Preferably, the second layer is positioned at a skin contact surface side with the wearer; and the first layer is positioned at a non-contact surface side of the wearer.

Preferably, the first layer is provided with a central aperture that is formed at a central part of the first layer in a widthwise direction W. The central aperture may have a longitudinally elongated shape extending along the lengthwise direction of the absorber. The central aperture may be formed across a crotch portion region, a foreside middle crotch region, and a backside middle crotch region. Preferably, the central aperture extends a greater distance into the foreside middle crotch region than into the backside middle crotch region. A length of the central aperture is preferably about 200 mm and a width thereof is preferably about 40 mm.

The central aperture may define the width of the central portion in the widthwise direction. Put differently, the central aperture may have the same width dimension as the central portion.

The first layer is preferably narrower in the width direction than the second layer, in the crotch portion region so that the second layer extends outwards beyond the first layer in the widthwise direction. The portion of the second layer, which extends outwards beyond the first layer may define the side edge portions.

The first layer is preferably substantially hourglass shaped with a narrow portion having a predetermined width in the widthwise direction; and a wide portion having a greater width in the widthwise direction than the narrow portion formed at each end of the narrow portion in the lengthwise direction; the second layer may have an overhang portion which extends outwardly further in the widthwise direction than the narrow portion; and a position in the lengthwise direction of the overhang portion may be superimposed on a position in the lengthwise direction of the narrow portion.

The rigidity of the wide portions of the first layer and the overhang portion of the second layer may be substantially identical.

Preferably, a pair of narrowed portions which are concave toward the central portion in the widthwise direction is formed at the side edges of the absorber; and the narrowed portions are positioned outside of the crotch portion region in the lengthwise direction.

Preferably, the central curve forming portion is formed of a central slit which is formed at the absorber along the lengthwise direction or a central elastic member which is disposed along the lengthwise direction.

The absorber may comprise a topside covering sheet, which is provided on a skin contact surface side, and a backside covering sheet, which is provided on a non-skin contact surface side of the absorber, wherein the topside covering sheet is bonded to the backside covering sheet at a portion at which one or more slits comprising the central curve forming portion and/or the side curve forming portions are formed.

Where a central elastic member is provided, this may be attached to the backside covering sheet.

Preferably the central elastic member is provided in alignment with the central aperture in the widthwise direction.

Preferably, the absorber is arranged such that when the central portion is curved, the elastic member is at least partially received within the central aperture.

Preferably, the side curve forming portion is formed of a side slit which is formed at the absorber along the lengthwise direction.

Where the absorber comprises first and second layers, preferably side slits are formed in both layers, which are superimposed over one another to form the side slits comprising the side curve forming portions.

Where a central aperture is provided, a length of the side slits is preferably smaller than that of the central aperture. Preferably, also, a width of the side slits is smaller than that of the central aperture.

The length of the side slits is preferably about 120 mm and the width thereof is preferably about 10 mm. It is preferable that the width of the side slit is 5 mm to 12 mm.

According to the embodiments in the above paragraphs, the features of which may be taken in isolation or in combination with one another, the advantageous effect(s) of the present invention is/are better ensured. Further advantageous effects of the respective embodiments may be obtained as discussed in the respective related descriptions.

Note that this application claims the benefit of Japanese Application No. 2010-043594 the entire disclosure of which is incorporated by reference herein.

The invention claimed is:
1. A disposable wearing article, comprising:
an absorber having:
a lengthwise direction;
a widthwise direction which is orthogonal to the lengthwise direction;
an inward direction which is adapted to be oriented toward a wearer; and
an outer direction which is oriented to a side opposite to the inward direction, wherein
the absorber has, in a crotch portion region adapted for application to a crotch portion of the wearer,
a central portion Which is formed at a central part of the absorber in the widthwise direction,
a pair of side edge portions including side edges of the absorber in the widthwise direction, and
a pair of middle portions which are positioned between the central portion and the side edge portions,
at the central portion, a central curve forming portion is formed along the lengthwise direction so that the absorber can be curved to be convex in the inward direction, at the middle portions, a pair of side curve forming portions are formed along the lengthwise direction so that the absorber can be curved to be convex in the outer direction, a top face of the absorber, which is formed to be convex in the inward direction by the central curve forming portion, is adapted to come into contact with the crotch portion, and a thickness of the absorber at the central portion is smaller than a thickness of the absorber at the middle portions, a thickness of the absorber at the side edge portions is smaller than the thickness of the absorber at the middle portions, the absorber has a first layer and a second layer superimposed on the first layer, the central portion and the side edge portions are formed of only the second layer, the middle portions are formed of the first layer and the second layer, the first layer is substantially hourglass shaped with
  a narrow portion having a predetermined width in the widthwise direction, and
  a wide portion formed at each end of the narrow portion hi the lengthwise direction, the wide portion having a greater width in the widthwise direction than the narrow portion, the second layer has an overhang portion which extends outwardly further in the widthwise direction than the narrow portion, and a position in the lengthwise direction of the overhang portion is superimposed on a position in the lengthwise direction of the narrow portion.

2. The disposable wearing article according to claim 1, wherein
  in the width direction, each of the middle portions includes an inside middle portion which is a region from the corresponding side curve forming portion to a boundary associated with the central portion,
  the central portion includes a sub-central portion which is a region from the boundary associated with the middle portion to the central curve forming portion in the widthwise direction, and
  a thickness of the absorber at the sub-central portion is smaller than a thickness of the absorber at the inside middle portion.

3. The disposable wearing article set forth in claim 1, wherein
  each of the middle portions includes an outside middle portion which is a region from the corresponding side curve forming portion to a boundary associated with the corresponding side edge portion in the widthwise direction, and
  a thickness of the absorber at the side edge portion is smaller than a thickness of the absorber at the outside middle portion.

4. The disposable wearing article according to claim 1, wherein each of the middle portions is formed, in the widthwise direction,
  from a position corresponding to half of a distance between a center of the central curve forming portion and a center of the corresponding side curve forming portion,
  to a position corresponding to half of a distance between the center of the corresponding side curve forming portion and the corresponding side edge of the absorber.

5. The disposable wearing article according to claim 2, wherein a width of the sub-central portion is identical to a width of the side edge portions in the widthwise direction.

6. The disposable wearing article according to claim 1, wherein:
  the second layer is positioned at a skin-contact surface side of the absorber; and
  the first layer is positioned at a non-skin-contact surface side of the absorber.

7. The disposable wearing article according to claim 1, wherein
  a pair of narrowed portions which are concave toward the central portion in the widthwise direction is formed at the side edges of the absorber, and
  the narrowed portions are positioned outside of the crotch portion region in the lengthwise direction.

8. The disposable wearing article according to claim 1, wherein the central curve forming portion is formed of
  a central slit which is formed at the absorber along the lengthwise direction, or
  a central elastic member which is disposed along the lengthwise direction.

9. The disposable wearing article according to claim 1, wherein each of the side curve forming portions is formed of a side slit which is formed at the absorber along the lengthwise direction.

* * * * *